United States Patent [19]
Ziaka et al.

[11] Patent Number: 6,090,312
[45] Date of Patent: *Jul. 18, 2000

[54] REACTOR-MEMBRANE PERMEATOR PROCESS FOR HYDROCARBON REFORMING AND WATER GAS-SHIFT REACTIONS

[76] Inventors: Zoe D. Ziaka; Savvas Vasileiadis, both of 1179 W. 37th St., Apt #D, Los Angeles, Calif. 90007

[ * ] Notice: This patent is subject to a terminal disclaimer.

[21] Appl. No.: 08/595,040

[22] Filed: Jan. 31, 1996

[51] Int. Cl.$^7$ ........................................................ C07C 1/02
[52] U.S. Cl. .......................... 252/373; 518/700; 518/703; 518/728; 423/418.2; 423/650; 423/652; 44/457; 44/530; 44/591
[58] Field of Search ..................................... 423/650, 652, 423/418.2; 95/41; 252/373, 376; 518/700, 703, 728; 44/457, 530, 591

[56] References Cited

U.S. PATENT DOCUMENTS

| | | | |
|---|---|---|---|
| 4,826,599 | 5/1989 | Bikson et al. | 210/500 |
| 5,183,482 | 2/1993 | Najjar et al. | 55/16 |
| 5,229,102 | 7/1993 | Minet et al. | 423/652 |

OTHER PUBLICATIONS

Rezac et al., Journal of Membrane Science, 93, 193–201, 1994.
S. Vasileiadis and Z. Zioka, paper 3186b, AICHE Annual Meeting, Miami Beach, Fl., 1998.
K. Toi, Y. Maeda and T. Tokuda, J. Appl. Polym. Sci., 28, 3589, 1983.

*Primary Examiner*—Sreeni Padmanabhan

[57] ABSTRACT

New process designs are presented for reforming reactions of steam with hydrocarbons (such as methane, natural gas, light hydrocarbon feedstocks with one to four carbon atoms in each molecule), also for the water gas shift reaction that is of steam with carbon monoxide; also for carbon dioxide reforming of hydrocarbons (such as methane, acidic natural gas, coal gas, landfill gas, light hydrocarbon feedstocks with one to four carbon atoms in each molecule), and the combined reaction of steam carbon dioxide with same hydrocarbons. The processes employ organic polymer, organic polymer-inorganic support, and inorganic membrane permeators for species separation, with the permeators placed after the reactors where the above named reactions take place. The membranes in permeators separate selectively the $H_2$ and $CO_2$ species exiting from the reactors from the non-permeated reactants and products. The reject streams coming out of permeators can be recycled into the inlet of the first reactors; these reject streams can be also fed to consecutively placed steam reforming and water gas shift reactors for further conversion to $H_2$ and $CO_2$ products. The separated $H_2$ and $CO_2$ in membrane permeate and from the secondary reactions of permeator reject streams, can be used for direct methanol synthesis, feed to molten carbonate fuel cells, and other chemical syntheses; after the removal of $CO_2$ from the mixture, pure hydrogen can be recovered and used in chemical syntheses and as fuel in fuel cells and power generation cycles.

20 Claims, 4 Drawing Sheets

REACTOR-MEMBRANE PERMEATOR PROCESS FOR HYDROCARBON REFORMING AND WATER GAS-SHIFT REACTIONS

TECHNICAL FIELD

This invention relates to improved process designs for hydrocarbon steam reforming, hydrocarbon carbon dioxide reforming, combined hydrocarbon steam carbon dioxide reforming, and water gas shift reactions, which include systems of catalytic reactors with consecutively placed membrane permeators for simultaneous separation through the membranes of the $H_2$ and $CO_2$ species of these reactions from non-permeating reactants and products. The efficiency of the processes is increased by having the non-permeating gases from the permeators to be recycled into first reactors for continuous reaction; the non-permeating gas streams can be also used in similar downstream reaction processes for further conversion to $H_2$ and $CO_2$ which products can be used effectively as a combined mixture or as pure $H_2$, after the $CO_2$ condensation, for special chemical synthesis and as fuels.

BACKGROUND OF THE INVENTION

Catalytic steam reforming of low carbon atom hydrocarbons (methane, natural gas, naphtha) and the water gas shift are the main routes for producing $H_2$ and synthesis gas, a $H_2$, CO mixture, for use as fuel and chemical synthesis. The $CO_2$-hydrocarbon reforming route and the combined steam and $CO_2$ hydrocarbon reforming route are also possible routes for production of $H_2$ and synthesis gas but their catalysis is much more sensitive to carbon deposition and further developments are needed in both catalysis and reactor design for large scale process operation.

The above are mostly endothermic processes (with the exception of the water gas shift which is slightly exothermic), and the necessary heat load into the reactor to run the reactions at the desired temperature range can be provided by burning hydrocarbons from waste and flue gases.

The usual catalysts for the hydrocarbon steam and $CO_2$ reforming reactions and the combined one, are nickel (Ni) based alloys enriched with earth metals to prevent coke deposition during reaction and are usually supported on oxides of alumina ($Al_2O_3$), titania ($TiO_2$), silica ($SiO_2$), and less often zirconia ($ZrO_2$); Ruthenium (Ru), Rhodium (Rh), Palladium (Pd), Platinum (Pt) metal structures mixed with earth metals can also be used. For the water gas shift reaction used catalysts are based on iron (Fe), zinc (Zn), chromium (Cr), copper (Cu), nickel (Ni), cobalt (Co) compositions enriched with earth metals which are supported on similar to the above supports.

The produced $H_2$ from the above reactions is usually separated in a consecutive pressure swing adsorption unit; the $CO_2$ is commonly separated by using absorption in alkaloamine solutions and molecular sieve type adsorbents.

The participating reactions are given below:

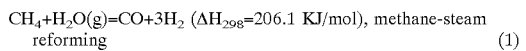

$CH_4+H_2O(g)=CO+3H_2$ ($\Delta H_{298}$=206.1 KJ/mol), methane-steam reforming (1)

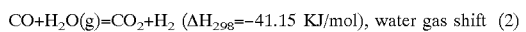

$CO+H_2O(g)=CO_2+H_2$ ($\Delta H_{298}$=−41.15 KJ/mol), water gas shift (2)

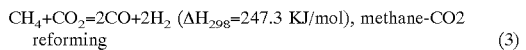

$CH_4+CO_2=2CO+2H_2$ ($\Delta H_{298}$=247.3 KJ/mol), methane-CO2 reforming (3)

Membrane permeators offer selective removal of specific gas products in a consecutive separation step. Membranes can be integrated within the reaction vessel itself to make permreactors (membrane reactors) which integrate reaction and separation in a single unit operation. Previous studies involve metal and ceramic membranes used in various types of high temperature catalytic reactions and processes related to hydrocarbon processing and conversion such as steam reforming, water gas shift and alkane dehydrogenations. Polymer membranes have been mostly used in gas and liquid separations at low to intermediate temperatures; as example, they have been used in purification of natural gas from $CO_2$, $H_2S$, $N_2$, halogens compounds. Membrane process designs can offer increased reactant conversions, product yields and product selectivities over other reaction-separation schemes such as reaction combined with adsorption, absorption, cryogenic separation, distillation and other separations. The selective product removal with the membrane can shift the equilibrium conversion to the product side and according to the mass conservation equation of a chemical reaction, the reactant conversion and subsequently the product yield can surpass the respective ones at equilibrium. Higher conversions and yields in membrane processes can make the processes to operate suitably at lower temperatures and increase their thermal efficiency and the life cycle of the catalyst and reactor wall materials, thereby reducing capital and operation costs.

U.S. Pat. No. 5,183,482 reports on separation of gas mixtures such as separation of $H_2$ from $CO_2$, $H_2$ from $N_2$, $H_2$ from He, by using inorganic aluminum alkoxide (ceramic) membranes. U.S. Pat. No. 5,229,102 reports on applications of catalytic alumina ceramic membrane reactors for steam hydrocarbon reforming with $H_2$ separation. U.S. Pat. No. 4,826,599 reports on methods for producing polymer membranes with permselective properties for separation of various gas mixtures. Earlier communications have reported on preparation and related gas separation applications of organic polymer and inorganic membranes and membrane based reactors.

In the aforementioned reports the objective is separation of a key product component (usually $H_2$) directly out of the reaction zone (in a membrane reactor case) or in a subsequent membrane process after the reactor (in a membrane permeator case). It is objective of this invention to provide hydrocarbon reforming and water gas shift processes involving organic polymer, organic polymer-inorganic supported membranes, and inorganic membranes which separate simultaneously $H_2$ and $CO_2$ gases from other compounds. The described membrane processes offer mass and thermal advantages over other reaction-separation schemes. As example, the proposed membrane processes can be successfully applied when the initial reactors (reforming or gas shift reactors) operate at low conversion reaction conditions and substantial amounts of reactants, which are not separated through the membranes, are recycled into initial reactor inlet or used in consecutive reactors in the same or different reactions. Moreover, direct utilization of the separated $H_2$ and $CO_2$ mixture can be in methanol synthesis and as feed in molten carbonate fuel cells for power generation; also after the $CO_2$ removal, the utilization of $H_2$ in chemical synthesis or as fuel are additional objectives of the invention. Utilization of the thermal load of the exiting from the reactor gases to generate steam to be used internally in steam reforming and water gas shift reactors, in an autothermic reactor mode, is an additional advantage of the invented processes.

SUMMARY OF THE INVENTION

The invention describes processes that convert gaseous hydrocarbons and hydrocarbon mixtures via steam reforming, carbon dioxide reforming, combined steam-carbon dioxide reforming, also carbon monoxide via the water gas shift reaction, to hydrogen, carbon monoxide and carbon dioxide products, depending on which reaction scheme takes place in the reactor, with the hydrogen and carbon dioxide to be separated in downstream membrane permeators, consecutively placed after the reactors. The membrane permeators consist of organic polymers, organic polymers on inorganic supports, and inorganic material membranes which are permselective to $H_2$ and $CO_2$ species in comparison to other reaction species. This specific permselective property of permreactors produces a $H_2$ and $CO_2$ rich stream in permeate, which can be used for direct methanol synthesis via the reaction: $CO_2+3H_2=CH_3OH+H_2O$, for direct feed to molten carbonate fuel cells via the following overall reaction: $H_2+CO_2+\frac{1}{2}O_2$ (cathode)$\rightarrow H_2O+CO_2$ (anode) and for $H_2$ generation after the $CO_2$ condensation. The finally produced $H_2$ can be used in chemical synthesis (such as methanol and ammonia synthesis, hydrogenation, hydrotreating and other reactions), and as fuel in power generation systems (such as gas and steam turbines, gas and jet type engines for power plants) and fuel cells (such as solid oxide, molten carbonate, alkaline, proton exchange, phosphoric acid). The exiting from the reactors gas mixture passes through a heat exchanger where it is cooled to a lower temperature which is the operating temperature of the permeator with the simultaneous condensation of the unreacted steam (gaseous water) from the mixture, and the generation of steam into the other side of the heat exchanger which steam can be fed into the inlet of the first reactor or into the inlet of consecutively placed, after the permeator, steam reforming and water gas shift reactors.

The exiting from the permeator reject (non-permeating) gases which are mainly unreacted hydrocarbons and carbon monoxide are recycled into the inlet of the initial reactors for continuous reaction or fed into consecutively placed catalytic reactors which are conducting hydrocarbon steam reforming and water gas shift reactions, for additional production of $H_2$ and $CO_2$ gases at the reactor exit.

The membrane permeators preferably consist of several thin hollow fibers or cylindrical tubes packed within a stainless steel module which have suitable inlet and outlet ports to deliver the gas permeated through the hollow fibers or tubes. The permeator can be also made from spiral wound membranes fabricated in a shell and tube configuration for the passage of feed and permeate gases respectively. Also, the permeator can be of a plate or disc configuration which includes a flat membrane creating two distinct sides for the feed and permeate streams.

Organic polymers can be fabricated as non-porous membranes and used as permeation materials; these polymers have high glass transition temperatures to withstand long term operation in permeator under extended temperature, pressure, and gas flow conditions. Polymers can be selected from the groups of polyimides, polycarbonates, polysulfones, polybenziimidazoles, polyphosphazenes, polyamides, polystyrenes, polycaprolactams, parylenes, polyvinyl halides, polyacetates, polysiloxanes, and other polymers with high glass transition temperature. Composites or copolymers of the above polymers made by more than one polymers can be also made and used as membranes. The hollow fibers or cylindrical tubes can be also made from thin top layers of organic polymer membranes supported on porous inorganic supports such as ceramic, glass and metallic cylindrical fibers or tubes.

Membranes which separate $H_2$ and $CO_2$ from other components can also be made by inorganic materials which include oxides of alumina, titania, silica, zirconia and various types of glass, in cylindrical hollow fiber and tube, plate and disc configurations. Similar permselective inorganic membranes can be also made by sols of the above inorganic oxides mixed with metals such as nickel, palladium, platinum, silver, gold, rhodium, ruthenium, rhenium, chromiun, cobalt, copper, zinc which metals can be provided in the form of various metal precursors or metal salts. The inorganic membranes are fabricated as thin layers in hollow fiber, tube type, or plate and disc configurations supported on inorganic porous supports of similar to the membrane geometrical shape. Also, thin top layer inorganic membranes can be supported on the same or different type of inorganic support materials.

Gas permeation through organic polymer membranes occurs with a combined mechanism of gas molecular diffusion and gas solution within the polymer; in inorganic membranes the main gas permeation mechanisms are various types of diffusion, that is molecular (Knudsen), bulk, surface, configurational, and of flow, that is convective, capillary depending on the pore size of the permeating gas molecule and the pore size of the inorganic permeable medium.

The invented process can be applied over a wide range of operating conditions for the reactors and the membrane permeators. The reactors can be of various vessel design such as catalytic fixed bed, plug flow, continuous stirred tank, fluidized bed and operate at various temperature and pressure conditions to produce exit gases at various hydrocarbon conversion and product yield levels. The reactors can be of same or different volumes and filled with the same or different weight of catalytic materials. Usual operating temperatures of the steam and $CO_2$ reforming and water gas shift reactors can be in the 200–800° C. range and pressures in the 1–50 atm with steam to hydrocarbon, and steam to CO feed ratios in the 1.0–7.0:1.0 range. Various feed compositions of $CH_4:CO_2$, and $CH_4:CO_2:H_2O$ can be used in the corresponding $CO_2$ reforming reactions without and with steam depending on the desired composition of the output from the reactor product mixture of synthesis gas which is CO and $H_2$.

The reactors in the described processes are catalytic with the catalyst to be loaded in form of pellets or particles within the reactor volume. Catalysts for the steam and $CO_2$ reforming reactions are of nickel (Ni), palladium (Pd), rhodium (Rh), ruthenium (Ru), platinum (Pt) compositions; for the water gas shift iron (Fe), zinc (Zn), chromium (Cr), copper (Cu), nickel (Ni), cobalt (Co) are used. These catalysis metals are either in the metal oxide or metal precursor form mixed with various earth metals (CaO, MgO, $La_2O_3$) and supported on oxides of alumina ($Al_2O_3$), titania ($TiO_2$), silica ($SiO_2$), zirconia ($ZrO_2$).

The organic polymer and organic polymer-inorganic support membrane permeators can operate usually between 35–500° C. depending on the limiting glass transition temperature of the polymer membranes and at pressures between 1–50 atm depending on the pressure of the preceded and following reactors. The operating temperature of the polymer permeators must be kept well below their polymer membrane glass transition temperature in order for the membrane to maintain constant permselective properties, that is constant permeability to $H_2$ and $CO_2$ and dimensional stability with time on gas stream. The temperature of the permeator must be also higher than the critical temperature of the gas mixture entered into the permeator after the steam condensation, that is mixture of unreacted hydrocarbons, CO, $CO_2$, $H_2$, in order to have a permeate mixture through the membrane in the gas state and not in vapor state, to avoid plasticization effects in the membrane with subsequent loss of its permselective properties (i.e., decrease in permeability and selectivity values of the permeating $H_2$ and $CO_2$ components) and its mechanical strength. Selectivity of the membrane in two permeating components is defined as the ratio of permeabilities of these components through the membrane. For the inorganic membranes higher temperatures in permeators can be used which may approach the temperature of the preceded reactor, depending also on the desired thermal design of the overall system. Inorganic materials such as those described above as membranes, usually withstand on higher temperatures and pressures than their usual polymer counterparts.

Various hydrocarbon feedstocks can be utilized in the proposed process designs for steam reforming and the water gas shift, with methane ($CH_4$) and carbon monoxide (CO) to be the primary feedstocks respectively. Constituents selected from the group of methane, ethane, propane, n-butane, i-butane, methanol, ethanol, CxHy type gaseous hydrocarbons with x=1–4 or mixtures of these gases, also natural gas, coal gas rich in $CH_4$, landfill gas rich in $CH_4$ can be used in the steam reforming process as substitute for $CH_4$.

Acidic natural gas rich in $CH_4$ and $CO_2$, coal gas rich in $CH_4$ and $CO_2$, landfill gas rich in $CH_4$ and $CO_2$, other refinery and flue gas mixtures rich in $CH_4$ and $CO_2$ can be used in the $CO_2$ reforming and the combined steam-$CO_2$ reforming process as a substitute for a pure $CH_4$ and $CO_2$ feed mixture. $CH_4$ can be also substituted with higher hydrocarbons as in the case of steam reforming.

The invented processes can offer higher overall reactant conversions and product yields with respect to conventional reactor-separator configurations, based on the in-line separative ability of the membranes to $H_2$ and $CO_2$, the capability for the in-line reactant recycling into the initial reactors, and the additional process capability for reactant conversion and utilization via the downstream placed reactors following the permeators. The invented processes can be generalized to include cascades of multiple reactors and membrane permeators in series and parallel configurations to maximize reactant conversion and product yield, also $H_2$, $CO_2$ direct utilization via the proposed processes, and the reactant recycling, utilization, and further conversion capacity.

The described processes are considered environmentally benign in terms of the in-situ $CO_2$ abatement via the $CO_2$ and the combined steam, $CO_2$ reforming reaction routes for conversion of $CO_2$ with hydrocarbon mixtures to valuable synthesis gas (CO, $H_2$) products.

DETAILED DESCRIPTION OF THE DRAWINGS

Figure 1:
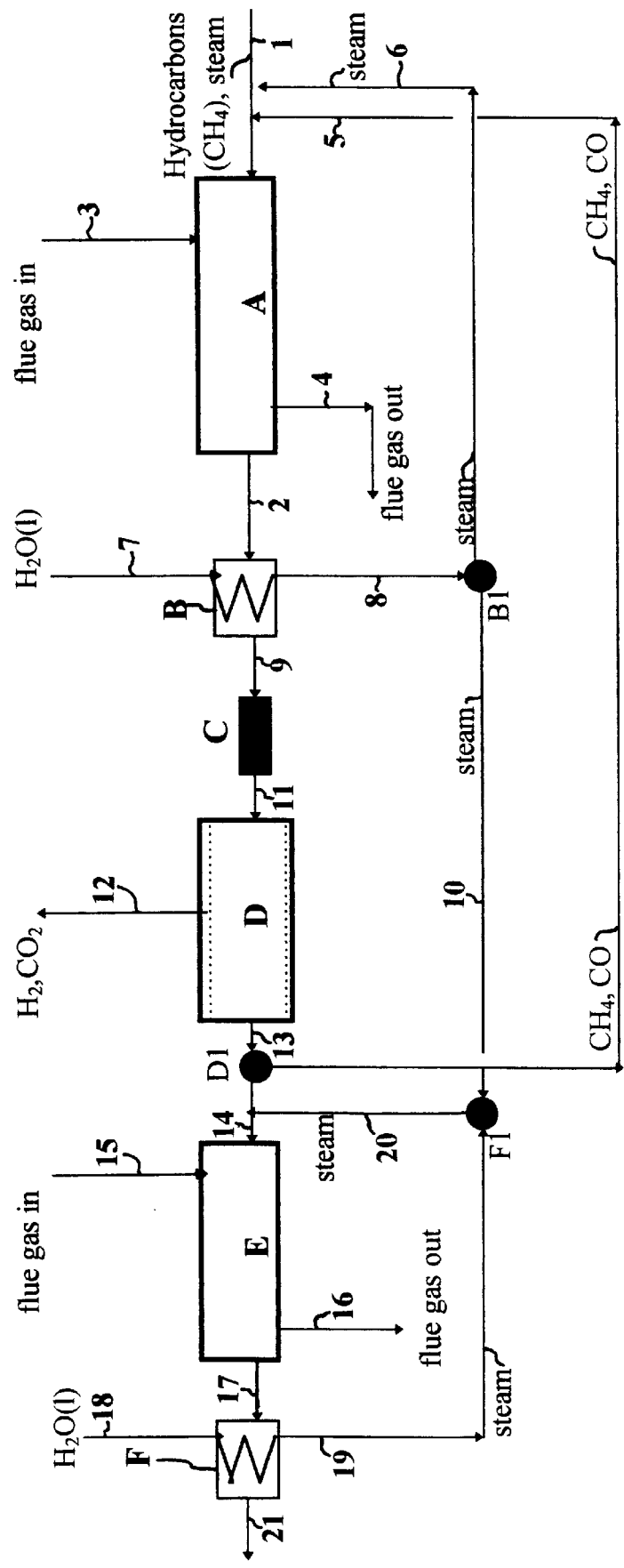
FIG. 1, shows a system (cascade) of a catalytic reactor for hydrocarbon steam reforming with a consecutive membrane permeator. The reject from the permeator stream containing non-permeated $CH_4$ and CO can be either recycled into the first reactor or fed into a subsequent catalytic steam reforming reactor.

In FIG. 1, stream 1 contains hydrocarbon feedstocks such as methane ($CH_4$) mixed with steam introduced in catalytic reactor A which is filled with catalyst particles to conduct the methane reforming reaction (1) and the simultaneously occurring water gas shift reaction (2). Some hydrogen may be added into stream 1, which can usually be between 1–15% of the feed volume, to depress carbon formation from methane cracking especially in the inlet of the reactor A. The reaction products $H_2$, CO and $CO_2$ together with the unreacted steam ($H_2O(g)$) and $CH_4$ are entered through stream 2 into heat exchanger B, where steam is removed through condensation, and by the heat exchanging process new steam is generated in stream 8 from the water of stream 7. Stream 8 can provide steam, that is $H_2O(g)$, in reactors A and E through streams 6 and 10 respectively in an alternative or simultaneous manner by use of valve B1. The steam in 8 aquires the exchanged heat load from stream 2, the hot gas effluent of reformer A, and thus its derived streams 6,10,20 can be mixed directly with streams 1 and 14 which are fed directly into reformers A and E respectively.

Steam from 8 is used via streams 10,20 and valve F1 to provide initial steam in reformer E. Stream 9 passes through a bed of particles (moisture adsorbent) C to remove any non-condensed traces of moisture and through exit stream 11 enters into membrane permeator D. Stream 11 has been cooled in temperature of permeator D and contains the $H_2$, CO, $CO_2$ and unreacted $CH_4$ gas species. $H_2$ and $CO_2$ are removed in permeate stream 12 through permselective action of membrane in D. Non permeating species $CH_4$ and CO exit from permeator through stream 13 which can be called a reject stream. Stream 13 can be recycled via valve D1 and stream 5 into the first reformer A for continuous reforming and conversion to $H_2$ and $CO_2$ products. Alternatively, by use of same valve D1, stream 13 becomes 14 which enters into the steam reformer E for additional reforming and shift reactions, via reactions (1) and (2), and conversion to final $H_2$, $CO_2$ products. Steam in reformer E is provided via stream 20. Unreacted steam is removed from exit stream 17 by passing this stream through heat exchanger F. Steam is generated from water of stream 18 and via streams 19,20 and valve F1, the steam is fed into inlet of reformer E. Stream 21 contains $H_2$, $CO_2$ products and traces of unreacted CO, $CH_4$ depending on the operating conditions, that is the temperature, pressure and feed composition of streams 14 and 20, of reformer E.

Steam reformers A and E are endothermic and flue gas streams 3,4 and 15,16 respectively are used to provide the necessary heat content to drive parallel reactions (1) and (2) to completion. The two reformers can operate at same or different temperature and pressure conditions.

Exit stream 21 can be used separately or it can be mixed with stream 12 to make a combined $H_2$ and $CO_2$ stream to be used for chemical synthesis or as fuel. The $H_2$, $CO_2$ product mixture can be used for direct methanol synthesis via the exothermic reaction: $3H_2+CO_2=CH_3OH(g)+H_2O$ (g). Also $H_2$, $CO_2$ can be used directly as feed to molten carbonate fuel cell units for electricity generation via the overall electrochemical reaction:

$H_2 + CO_2 + \frac{1}{2}O_2$ (cathode) → $H_2O + CO_2$ (anode)

Alternatively, $CO_2$ can be condensed cryogenically from the binary mixture, and the final $H_2$ product can be used for chemical synthesis such as methanol, ammonia synthesis, hydrotreating and hydrogenation of oil, petroleum and hydrocarbon feedstocks. $H_2$ can be used also as fuel in gas turbine, conventional and jet type gas engines for power plants, either pure or mixed with various combustible hydrocarbons. $H_2$ can also be used as fuel in the anode of various types of fuel cells such as phosphoric, molten carbonate, solid oxide, proton exchange, alkaline and other types. Thereby, the invented process can provide fuel in the form of $H_2$ to be used in engine designs for transportation vehicles such as automobiles and aircrafts and in stationary power generation cycles, by using fuel cells and microturbine parts and configurations.

The described process is able to overcome the equilibrium $CH_4$ reactant conversion limitations through the intermediate removal of $H_2$ and $CO_2$ products from exit reformed gases, in permeator D. Thus, the process increases $CH_4$ conversion and $H_2$, $CO_2$ yields above those obtained in conventional reaction separation systems, such as those using separation of $H_2$ with pressure swing adsorption and of $CO_2$ with microporous adsorbents and by absorption in liquid solutions. The calorific value of the obtained $H_2$, $CO_2$ product mixture is higher that this of the reactants $CH_4$ and steam and the endothermic heat of reaction is stored in the products which can be subsequently used as fuel or in chemical synthesis.

Assuming 100% conversion of reactions (1) and (2), 1 mol of $CH_4$ (with heat of combustion: 212.8 kcal) and 2 mol of $H_2O(g)$ (with no heat of combustion) generate 1 mol of $CO_2$ (with no heat of combustion) and 4 mol of $H_2$ (with heat of combustion: 273.3 kcal). These values are at 25° C. This corresponds to about 28% increase in calorific value for the product gases. By providing external heat through flue or waste gas input in the reformers and with the described two heat exchangers in place, the energy requirement of the reactor-permeator cascade is fulfilled and the process operates in a thermally independent manner providing for an energy efficient design.

Figure 2:
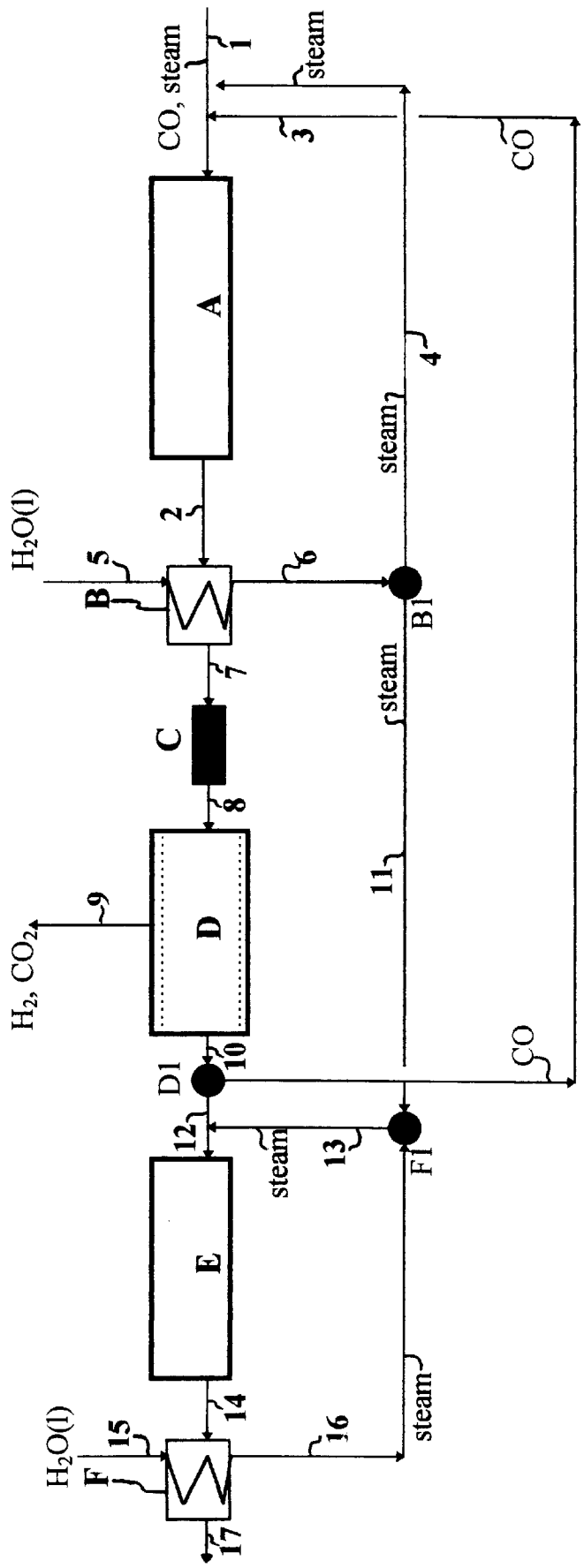
FIG. 2, shows a similar reactor permeator system applied for the water gas shift reaction. The reject from the permeator CO stream is recycled into the initial catalytic shift reactor or fed into a subsequent catalytic shift reactor.

In FIG. 2, stream 1 contains carbon monoxide (CO) mixed with steam introduced in catalytic reactor A which is filled with catalyst particles to conduct the water gas shift reaction (2). The reaction products $H_2$, $CO_2$ together with the unreacted steam ($H_2O(g)$) and CO are entered through stream 2 into heat exchanger B, where steam is removed through condensation, and by the heat exchanging process new steam is generated in stream 6 from liquid water of stream 5. Stream 6 can provide steam in shift reactors A and E through streams 4 and 11,13 respectively, in an alternative or simultaneous manner by use of valve B1 and F1. The steam in 6 acquires the exchanged heat load from the hot gas effluent in 2, and thus derived streams of steam 4,11,13 can be mixed directly with streams 1 and 12 which are fed into reactors A and E respectively.

Steam from 6 is used via streams 11,13 and valve F1 to provide initial steam in reactor E. Stream 7 passes through a bed of particles (moisture adsorbent) C to remove any non-condensed traces of moisture and through exit stream 8 enters into membrane permeator D. Stream 8 contains products $H_2$, $CO_2$ and unreacted CO gas species and has been cooled at the temperature of permeator D. H2 and $CO_2$ are removed in permeate stream 9 through permselective action of membrane in D. Non permeating CO exits from permeator through stream 10 which can be called a reject stream. Stream 10 can be recycled via valve D1 and stream 3 into the first shift reactor A for continuous shift reaction and conversion to $H_2$ and $CO_2$ products. Alternatively, by use of same valve D1, stream 10 becomes 12 which enters into E for additional shift reaction (2), and conversion to final $H_2$, $CO_2$ products. Steam in E is provided via stream 13. Unreacted steam is removed from exit stream 14 by passing this stream through heat exchanger F. New steam is generated from water of stream 15 and via streams 16,13 and valve F1 is fed into inlet of reactor E. Exit stream 17 contains $H_2$, $CO_2$ products and traces of unreacted CO depending on the operating conditions, that is the temperature, pressure and feed composition of streams 12 and 13, of reactor E.

Shift reactors A and E are exothermic and no heat input is necessary as with the previous endothermic reformers in process of FIG. 1. Stream 1 needs to be preheated in temperature of reactor A before entering into reactor. By use of the heat content of streams 2 and 14, which are exiting from the reactors, to provide heat to inlet streams 4 and 13 entering into reactors, the entire process operates in an autothermic manner with no additional heat input necessary. The two shift reactors can operate at same or different temperature and pressure conditions.

Exit stream 17 can be used separately or it can be mixed with stream 9 to make a combined $H_2$ and $CO_2$ stream to be used for chemical synthesis or as fuel in applications similar to the ones mentioned above for the methane steam reforming reactors. Pure $H_2$ can be recovered after the $CO_2$ condensation and used as fuel or in chemical synthesis.

The described shift process is able to overcome the equilibrium CO reactant conversion limitations, through intermediate removal of $H_2$ and $CO_2$ products in permeator D. Thus, the process increases CO conversion and $H_2$, $CO_2$ yields above those obtained in conventional reaction separation systems for production of $H_2$ and $CO_2$. The calorific value of the obtained $H_2$, $CO_2$ product mixture is increased by about 1% from this of the reactants CO and steam. By use of the two heat exchangers each shift reactor operates in an autothermic manner with no need of additional heat load in the system except for the initial preheating of stream 1 to start-up operation in reactor A.

Figure 3:
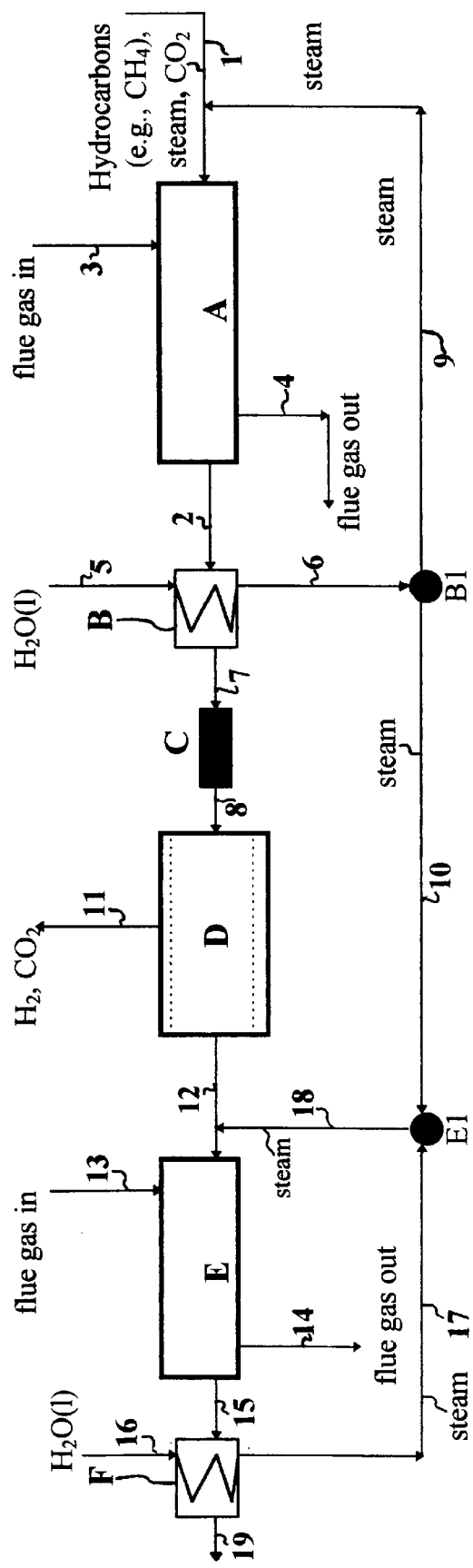
FIG. 3, shows a similar reactor permeator system applied for the hydrocarbon combined steam and $CO_2$ reforming reaction. Recycling of the permeator reject is not applied in this case, and this stream is reformed with steam in a subsequent catalytic reformer.

In FIG. 3, stream 1 contains hydrocarbon feedstocks such as methane ($CH_4$) mixed with steam and carbon dioxide ($CO_2$) introduced in catalytic reactor A which is filled with catalyst particles to conduct the methane steam reforming reaction (1) and the simultaneously occuring methane $CO_2$ reforming reaction (3). The reverse of water gas shift, that is reaction (2) from right to left, may also occur in reactor A producing CO and $H_2O(g)$. Some hydrogen may be added into stream 1, that is usually between 1–15% of feed volume, to depress carbon formation from methane cracking especially in the inlet of reactor A. The reaction products $H_2$, CO together with the unreacted steam ($H_2O(g)$), $CO_2$ and $CH_4$ are entered through stream 2 into heat exchanger B, where steam is removed through condensation, and by the heat exchanging process new steam is generated in stream 6 from the water of stream 5. Stream 6 can provide steam in reactors A and E through streams 9 and 10,18 respectively in an alternative or simultaneous manner by use of valves B1,E1. The steam in 6 acquires the exchanged heat load from stream 2, the hot gas effluent of reformer A, and thus its derived streams 9,10,18 can be mixed directly with streams 1 and 12 which are fed directly into reformers A and E respectively.

Steam from 6 is used via streams 10,18 and valves B1,E1 to provide initial steam in reformer E. Stream 7 passes through a bed of particles (moisture adsorbent) C to remove any non-condensed traces of moisture and through exit stream 8 enters into membrane permeator D. Stream 8 contains the $H_2$, CO products and unreacted $CH_4$, $CO_2$ gases and has been cooled at the temperature of permeator D. $H_2$ and the $CO_2$ are removed in permeate stream 11 through permselective action of membrane in D. Non permeating species $CH_4$ and CO exit from permeator through stream 12 which is the reject stream and enters into the steam reformer E for steam reforming and water shift reactions, which are reactions (1) and (2), and conversion to final $H_2$, $CO_2$ products. Steam in reformer E is provided via stream 18. Unreacted steam is removed from exit stream 15 by passing this stream through heat exchanger F. Steam is generated from water of stream 16 and via streams 17,18 and valve E1, steam is fed into inlet of reformer E. Exit stream 19 contains $H_2$, $CO_2$ products and traces of unreacted CO, $CH_4$ depending on the operating conditions, that is the temperature, pressure and feed composition of streams 12 and 18, of reformer E.

Reformers A and E are endothermic and flue gas streams 3,4 and 13,14 respectively are used to provide the necessary heat content to drive parallel reactions (1), (3) and (1),(2) respectively to completion. The two reformers can operate at same or different temperature and pressure conditions.

If conversion is high in reformer A under operating conditions the product in stream 2 is mainly CO and $H_2$ and can be used directly as synthesis gas in methanol synthesis via the direct exothermic reaction: $CO+2H_2=CH_3OH$, also in Fischer Tropsch reactions for production of gasoline type hydrocarbons, and as fuel in gas turbines and engines for power plant cycles. If the entire process takes place with two reformers and the permeator, the final $H_2$,$CO_2$ exit stream 19 can be used separately or it can be mixed with stream 11 to make a combined $H_2$ and $CO_2$ stream to be used for chemical synthesis or as fuel, as also described earlier with the applications of the steam reforming process in FIG. 1. Alternatively, $CO_2$ can be condensed cryogenically from the binary mixture, and the final $H_2$ product can be used for chemical synthesis or as fuel in fuel cells, gas turbines and engines for power generation in transportation (automobile, aircraft) and stationary applications.

The described process is able to overcome the equilibrium $CH_4$ and $CO_2$ reactant conversion limitations, through the intermediate removal of $H_2$ and $CO_2$ gases from exit reformed stream, in permeator D. Also, the process can convert CO and $CH_4$ to $H_2$ and $CO_2$ final products. The calorific value of the obtained $H_2$, $CO_2$ product mixture is higher that this of the reactants $CH_4$, $CO_2$ and steam and the endothermic heat of reaction is stored in the products which can be used subsequently as fuel or in chemical synthesis.

Assuming 100% conversion of reactions (1) and (3), 2 mol of $CH_4$ (with heat of combustion: 425.6 kcal), 1 mol of $CO_2$ (with no heat of combustion), and 1 mol of $H_2O(g)$ (with no heat of combustion), produce 3 mol of CO (with heat of combustion: 202.8 kcal) and 5 mol of $H_2$ (with heat of combustion: 341.5 kcal). These values are at 25° C. This corresponds to about 28% increase in calorific value for the product. External heat can be provided in reformers A and E through flue or waste gas and the energy requirements of the reactor-permeator cascade is fulfilled in an independent manner providing for an energy efficient design.

Figure 4:
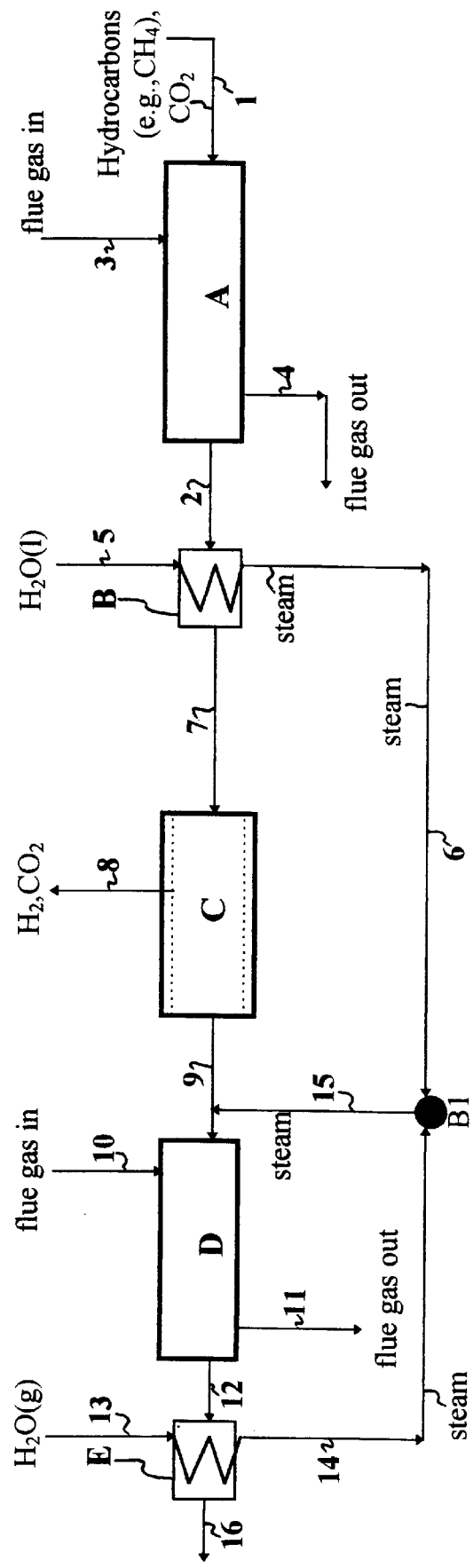
FIG. 4, shows a similar reactor permeator system applied for the hydrocarbon $CO_2$ reforming reaction. In this process, steam is not used in the first reactor feed, and the design of equipment becomes simpler. Recycling of the permeator reject is not applied, and this stream is reformed with steam in a subsequent catalytic reformer.

In FIG. 4, stream 1 contains hydrocarbon feedstocks such as methane ($CH_4$) mixed with carbon dioxide ($CO_2$) introduced in catalytic reactor A which is filled with catalyst particles to conduct the methane-carbon dioxide reforming reaction (3). The reverse of water gas shift, that is reaction (2) from right to left, may also occur in reactor A producing CO and $H_2O(g)$. Some hydrogen may be added into stream 1, to depress carbon formation from methane cracking especially in the inlet of reactor A, that is usually between 1–15% of the feed volume. The reaction products $H_2$, CO, and $H_2O(g)$ traces together with unreacted $CO_2$ and $CH_4$ are entered through stream 2 into heat exchanger B, where steam is generated in stream 6 from the water of stream 5 and any steam in stream 2 is condensed by the cooling of stream 2. Stream 6 can provide steam in reformer D through stream 15 by use of valve B1. The steam in 6, acquires the exchanged heat load from stream 2, the hot gas effluent of reformer A, and thus its derived stream 15 can be mixed directly with stream 9 which is fed into reformer D. Steam from 6 is used to provide initial steam flow in reformer D.

Stream 7 exiting the heat exchanger has been cooled at the temperature of permeator C. Stream 7 contains the $H_2$, CO products and unreacted $CH_4$, $CO_2$ gases. $H_2$ and $CO_2$ are removed in permeate stream 8 through permselective action of membrane in C. Non permeating species $CH_4$ and CO exit from permeator through stream 9 which is the reject stream entering into steam reformer D for steam reforming and water shift reactions (1) and (2), and conversion to final $H_2$, $CO_2$ products. Unreacted steam is removed from exit stream 12 by passing this stream through heat exchanger E. Steam is generated from water of stream 13 and via streams 14,15 and valve B1, steam is fed into inlet of reformer D. Exit stream 16 contains $H_2$, $CO_2$ products and traces of unreacted CO, $CH_4$ depending on the operating conditions, that is the temperature, pressure and feed composition of streams 9 and 15, of reformer D.

Reformers A and D are endothermic and flue gas streams 3,4 and 10,11 respectively are used to provide the necessary heat content to drive reactions (3) and (1),(2) respectively to completion. The two reformers can operate at same or different temperature and pressure conditions.

If conversion is high in reformer A under operating conditions the product in stream 2 is mainly CO and $H_2$ which can be used directly as synthesis gas for methanol synthesis as described in previous process (FIG. 3), Fischer Tropsch reactions for production of gasoline type hydrocarbons, and as fuel in gas turbines and engines for power plant cycles. If the entire process takes place with two reformers and the permeator, the final $H_2$, $CO_2$ exit stream 16 can be used separately or it can be mixed with stream 8 to make a combined $H_2$ and $CO_2$ stream to be used for chemical synthesis or as fuel as described earlier with the applications of the reforming and shift processes in FIGS. 1,2,3. Alternatively, a final $H_2$ product can be recovered after the $CO_2$ condensation, and produced $H_2$ can be used for chemical synthesis or as fuel in same applications with those described earlier.

The described process is able to overcome equilibrium $CH_4$ and $CO_2$ reactant conversion limitations, through the intermediate removal of $H_2$ and $CO_2$ gases in permeator D. Also, the process can further convert CO and $CH_4$ to $H_2$ and $CO_2$ final products. The calorific value of the obtained $H_2$, $CO_2$ product mixture is higher that this of the reactants $CH_4$ and $CO_2$, and the endothermic heat of reaction is stored in the products which can be used subsequently as fuel or in chemical synthesis.

Assuming 100% conversion of reaction (3), 1 mol of $CH_4$ (with heat of combustion: 212.8 kcal) and 1 mol of $CO_2$ (with no heat of combustion), produce 2 mol of CO (with heat of combustion: 135.2 kcal) and 2 mol of $H_2$ (with heat of combustion: 136.6 kcal). The values are at 25° C. This corresponds to about 28% increase in calorific value for the product. External heat can be provided in reformers A and E through combustion of flue or waste gas and the energy requirements of the reactor-permeator cascade is fulfilled in an independent manner providing for an energy efficient design.

We claim:

1. A process that reforms a hydrocarbon with steam ($H_2O(g)$) over a bed of metallic catalyst in a steam reforming reactor to produce $H_2$, $CO_2$ and $CO$ by the hydrocarbon steam reforming and water gas shift reactions, with the exit stream to be passed through a heat exchanger to reduce its temperature and condense the unreacted steam by generating new steam in other side of the exchanger to be used as feed into this reforming reactor and any subsequently placed reformer, with the remaining gas mixture to remove moisture traces by passage through a bed of moisture adsorbing particles, with the dry cooled exit mixture from the particle bed to enter into a membrane permeator made by one of the following materials, organic polymer membrane, organic polymer membrane-inorganic support, inorganic membrane, which all materials are permselective to $H_2$ and $CO_2$ and separate these two species from the unreacted hydrocarbon and $CO$, with these last non-permeating compounds to exit from the non-permeate side of the permeator as a reject stream, with the $H_2$ and $CO_2$ permeate product mixture to be used for chemical synthesis and as fuel either as is a mixture or as pure $H_2$ after the $CO_2$ condensation and removal.

2. The process of claim 1 wherein the hydrocarbon is a single constituent or a mixture of constituents of the following components methane, ethane, propane, n-butane, i-butane, methanol, ethanol, natural gas rich in methane, coal gas rich in methane, landfill gas rich in methane, flue gas rich in methane.

3. The process of claim 1 wherein the membrane in permeator is made from an organic polymer or composite or copolymer of organic polymers selected from the group of polyimides, polycarbonates, polysulfones, polybenziimidazoles, polyphosphazenes, polyamides, polystyrenes, polycaprolactams, parylenes, polyvinyl halides, polyacetates, polysiloxanes or from inorganic-metal composites based on pure or mixture of one of the following ceramic oxides:

alumina ($Al_2O_3$), titania ($TiO_2$), silica ($SiO_2$), zirconia ($ZrO_2$).

4. The process of claim 1 with the reject stream from the permeator containing unreacted $CO$ and hydrocarbon to be recycled into the inlet of the first reformer for continuous steam reforming and water gas shift reactions in the reformer.

5. The process of claim 1 with the reject stream from the permeator containing unreacted hydrocarbon and $CO$ to enter into a consecutively placed steam reformer to react with steam over a bed of metallic catalyst via the steam reforming and water gas shift reactions and be converted into $H_2$ and $CO_2$ product, having this exit stream from last reformer to condense its unreacted steam by passage through a heat exchanger and by generating new steam in other side of the heat exchanger to be used as feed in the inlet of the last reformer, having the final exit dry mixture of $H_2$ and $CO_2$ from the heat exchanger to be combined with the permeate from the membrane permeator, $H_2$ and $CO_2$ stream, to make one combined stream of $H_2$ and $CO_2$ to be used for chemical synthesis, also as fuel either as a mixture or as pure $H_2$ after the $CO_2$ condensation and removal.

6. The process of claim 5 wherein the combined $H_2$ and $CO_2$ product mixture is used (a) for direct methanol synthesis via the reaction: $CO_2 + 3H_2 = CH_3OH(g) + H_2O(g)$, (b) for direct feed in molten carbonate fuel cell (MCFC) units for electricity generation via the overall electrochemical reaction: $H_2 + CO_2 + \frac{1}{2}O_2(\text{cathode}) \rightarrow H_2O + CO_2(\text{anode})$, (c) for other $CO_2$ and $H_2$ or $H_2$ only chemical synthesis reactions, moreover after the removal of $CO_2$ pure $H_2$ is used (d) as fuel in the anode of fuel cells such as phosphoric acid, alkaline, molten carbonate, solid oxide, proton exchange, (e) and as fuel in gas turbines, conventional and jet type gas engines.

7. The process of claim 1 with the hydrocarbon in stream 1 to be replaced by carbon monoxide ($CO$) to react with steam in reactor A via only the water gas shift reaction, with the exit from reactor stream to contain products $H_2$, $CO_2$ and unreacted $CO$ and steam, having steam condensation and removal of moisture content in heat exchanger and moisture adsorbing particle bed, having the $H_2$ and $CO_2$ separated in the consecutive membrane permeator and the $CO$ exiting from the non-permeate side of the permeator as reject stream, with the $H_2$ and $CO_2$ mixture permeated from membrane permeator to be used for chemical synthesis, also as fuel either as a mixture or as pure $H_2$ after the $CO_2$ condensation and removal.

8. The process of claim 7 with the reject stream from the permeator containing the unreacted $CO$ to be recycled into inlet of first water gas shift reactor for continuous reaction into the reactor.

9. The process of claim 7 with the reject stream from the permeator containing unreacted $CO$ to enter into a consecutive placed water gas shift reactor to react with steam over a bed of metallic catalyst via the water gas shift reaction and be converted into $H_2$ and $CO_2$ product, having the exit stream from last shift reactor to condense its unreacted steam by passage through a heat exchanger and by generating new steam in the other side of the heat exchanger to be used as feed in the inlet of this last shift reactor in an autothermic operation, having the final exit dry mixture of $H_2$ and $CO_2$ from last heat exchanger to be combined with the permeate from the membrane permeator, $H_2$ and $CO_2$ stream, to make one combined stream of $H_2$ and $CO_2$ to be used for chemical synthesis, also as fuel either as a mixture or as pure $H_2$ after the $CO_2$ condensation and removal.

10. A process that reacts a hydrocarbon with $CO_2$ and steam ($H_2O(g)$) over a bed of metallic catalyst in a steam and $CO_2$ reforming reactor to produce $H_2$ and CO via the hydrocarbon steam reforming reaction, the hydrocarbon $CO_2$ reforming reaction, and the reverse water gas shift reaction, with the exit stream to be passed through a heat exchanger to reduce its temperature and condense unreacted and produced steam by generating new steam in other side of the exchanger which is used as feed into this reforming reactor and any subsequently placed reformer, with the exit stream from the heat exchanger to be passed through a bed of moisture adsorbing particles to remove any moisture content, with the dry cooled exit gas mixture to enter into a membrane permeator made by one of the following materials, organic polymer membrane, organic polymer membrane-inorganic support, inorganic membrane, which all materials are permselective to $H_2$ and $CO_2$ and separate these two species in permeate stream from the unreacted hydrocarbon and product CO which exit from the non-permeate side of the permeator as a reject stream, with the $H_2$ and $CO_2$ permeate product mixture to be used for chemical synthesis, also as fuel either as a mixture or as pure $H_2$ after the $CO_2$ condensation and removal.

11. The process of claim 10 with the reject stream from the permeator containing unreacted hydrocarbon and CO to enter into a consecutively placed steam reformer to react with steam over a bed of metallic catalyst via the steam reforming and water gas shift reactions and be converted into $H_2$ and $CO_2$ products, having this exit stream from last reformer to condense its unreacted steam by passage through a heat exchanger and by generating new steam in other side of the heat exchanger which is used as feed in the inlet of this last reformer, having the final exit dry mixture of $H_2$ and $CO_2$ from the heat exchanger to be combined with the permeate from the membrane permeator, $H_2$ and $CO_2$ stream, to make one combined stream of $H_2$ and $CO_2$ to be used for chemical synthesis, also as fuel either as a mixture or as pure $H_2$ after the $CO_2$ condensation and removal.

12. The process of claim 10 wherein the membrane in the permeator is made from an organic polymer or composite or copolymer of organic polymers selected from the group of polyimides, polycarbonates, polysulfones, polybenziimidazoles, polyphosphazenes, polyamides, polystyrenes, polycaprolactams, parylenes, polyvinyl halides, polyacetates, polysiloxanes or from inorganic-metal composites based on pure or mixture of one of the following ceramic oxides:

alumina ($Al_2O_3$), titania ($TiO_2$), silica ($SiO_2$), zirconia ($ZrO_2$).

13. The process of claim 10 wherein the hydrocarbon is a single constituent or a mixture of constituents of the following components methane, ethane, propane, n-butane, i-butane, methanol, ethanol, natural gas rich in methane, coal gas rich in methane, landfill gas rich in methane, flue gas rich in methane.

14. The process of claim 10 wherein the feed hydrocarbon and $CO_2$ gases are substituted by a $CH_4$ and $CO_2$ mixture, acidic natural gas rich in $CH_4$ and $CO_2$, coal gas rich in $CH_4$ and $CO_2$, landfill gas rich in $CH_4$ and $CO_2$, other refinery and flue gas mixtures rich in $CH_4$ and $CO_2$.

15. A process that reacts a hydrocarbon with $CO_2$ over a bed of metallic catalyst in a $CO_2$ reforming reactor to produce $H_2$ and CO via the hydrocarbon $CO_2$ reforming reaction and the reverse water gas shift reaction, with the exit stream to be passed through a heat exchanger to reduce its temperature and condense any produced steam by generating new steam in other side of the exchanger, which steam can be used as feed into subsequently placed steam reformers, with the exit dry and cooled stream from the heat exchanger to enter into a membrane permeator made by one of the following materials, organic polymer membrane, organic polymer membrane-inorganic support, inorganic membrane, which all materials are permselective to $H_2$ and $CO_2$ and separate these two species through the permeate stream from the unreacted hydrocarbon and product CO which exit from the non-permeate side of the permeator as a reject stream, with the $H_2$ and $CO_2$ permeate product mixture to be used for chemical synthesis, also as fuel either as a mixture or as pure $H_2$ after the $CO_2$ condensation and removal.

16. The process of claim 15 with the reject stream from the permeator containing unreacted hydrocarbon and CO to enter into a consecutively placed steam reformer to react with steam over a bed of metallic catalyst via the steam reforming and water gas shift reactions and be converted into $H_2$ and $CO_2$ product, having this exit stream from last reformer to condense its unreacted steam by passage through a heat exchanger and by generating new steam in the other side of the heat exchanger to be used as feed in the inlet of the last reformer, having the final exit dry mixture of $H_2$ and $CO_2$ from the heat exchanger to be combined with the permeate from the membrane permeator, $H_2$ and $CO_2$ stream, to make one combined stream of $H_2$ and $CO_2$ to be used for chemical synthesis, also as fuel either as a mixture or as pure $H_2$ after the $CO_2$ condensation and removal.

17. The process of claim 15 wherein the membrane in the permeator is made from an organic polymer or composite or copolymer of organic polymers selected from the group of polyimides, polycarbonates, polysulfones, polybenziimidazoles, polyphosphazenes, polyamides, polystyrenes, polycaprolactams, parylenes, polyvinyl halides, polyacetates, polysiloxanes or other organic polymer, composite, copolymer with glass transition temperature above 50° C., also from inorganic materials and inorganic-metal composites based on pure or mixture of one of the following ceramic oxides:

alumina ($Al_2O_3$), titania ($TiO_2$), silica ($SiO_2$), zirconia ($ZrO_2$).

18. The process of claim 15 wherein the hydrocarbon is a single constituent or a mixture of constituents of the following components methane, ethane, propane, n-butane, i-butane, methanol, ethanol, natural gas rich in methane, coal gas rich in methane, landfill gas rich in methane, flue gas rich in methane.

19. The process of claim 15 wherein the feed hydrocarbon and $CO_2$ gases are substituted by a $CH_4$ and $CO_2$ mixture, acidic natural gas rich in $CH_4$ and $CO_2$, coal gas rich in $CH_4$ and $CO_2$, landfill gas rich in $CH_4$ and $CO_2$, other refinery and flue gas mixtures rich in $CH_4$ and $CO_2$.

20. The process of claim 16 wherein the combined $H_2$ and $CO_2$ product mixture is used (a) for direct methanol synthesis via the reaction: $CO_2 + 3H_2 = CH_3OH(g) + H_2O(g)$, (b) for direct feed in molten carbonate fuel cell (MCFC) units for electricity generation via the overall electrochemical reaction: $H_2 + CO_2 + \frac{1}{2}O_2(\text{cathode}) \rightarrow H_2O + CO_2(\text{anode})$, (c) for other $CO_2$ and $H_2$ or $H_2$ only chemical synthesis reactions moreover after the removal of $CO_2$ pure $H_2$ is used (d) as fuel in anode of fuel cells such as phosphoric acid, alkaline, molten carbonate, solid oxide, proton exchange, (e) and as fuel in gas turbines, conventional and jet type gas engines.

* * * * *